US00PP36828P2

(12) United States Plant Patent
Vele

(10) Patent No.: US PP36,828 P2
(45) Date of Patent: Jul. 15, 2025

(54) ***ALSTROEMERIA* PLANT NAMED 'Turcal139'**

(50) Latin Name: *Alstroemeria hybrida*
Varietal Denomination: Turcal139

(71) Applicants: Ernest Turc S.A.S, Angers (FR); Pierre Turc S.A.R.L., Maze-Milon (FR)

(72) Inventor: Mathieu Vele, Angers (FR)

( * ) Notice: Subject to any disclaimer, the term of this patent is extended or adjusted under 35 U.S.C. 154(b) by 0 days.

(21) Appl. No.: 18/985,322

(22) Filed: Dec. 18, 2024

(51) Int. Cl.
*A01H 5/02* (2018.01)
*A01H 6/00* (2018.01)

(52) U.S. Cl.
USPC ..... Plt./309

(58) Field of Classification Search
USPC ..... Plt./309
See application file for complete search history.

*Primary Examiner* — Susan McCormick Ewoldt
(74) *Attorney, Agent, or Firm* — Cassandra Bright

(57) ABSTRACT

A new and distinct cultivar of *Alstroemeria* plant named 'Turcal139' is disclosed, characterized by uniquely low growing/compact plants with excellent pot and garden performance. Plants are very floriferous with a long flowering period from June to October. Flowers are pink/salmon with a yellow center. Hardiness to −12° C. has been observed. Foliage is healthy and green, also during the flowering period. The new variety is an *Alstroemeria*, typically produced as an outdoor ornamental plant.

2 Drawing Sheets

Latin name of the genus and species: *Alstroemeria hybrida.*

Variety denomination: 'TURCAL139'.

BACKGROUND OF THE INVENTION

The new cultivar is the product of an open-pollination conducted by the inventor at a nursery in Mazé-Milon, France during May of 2012. The seed parent is the unpatented proprietary *Alstroemeria hybrida* referred to as '10001'. The pollen parent is the unpatented proprietary *Alstroemeria hybrida* referred to as '10005'. The new cultivar 'TURCAL139' was selected by the inventor in 2016 at the same location in Mazé-Milon, France.

The first asexual reproduction was performed by tissue culture in 2016, at the same nursery in Mazé-Milon, France. The inventor continued controlled testing and propagation, assessing stability of the unique characteristics of this variety. Multiple generations have been reproduced and have shown that the unique features of this cultivar are stable and reproduced true to type.

The inventor has filed an application with the CPVO Aug. 27, 2020, having application number 2020/1768. 'Turcal139' was not sold until 2024 due to a lack of commercial propagative material and distribution. The first sale was directly or indirectly from the inventor. This disclosure falls within the exception allowed under 102(b)(1).

SUMMARY OF THE INVENTION

The cultivar 'TURCAL139' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TURCAL139.' These characteristics in combination distinguish 'TURCAL139' as a new and distinct *Alstroemeria* cultivar:

1. Dwarf/compact plant that stays very low.
2. Excellent pot and garden performance.
3. Long flowering period from June to October.
4. Sturdy growth without floppy stems.
5. Very floriferous producing a salmon/pink flower with a yellow center.
6. Healthy green foliage, also during flowering period.
7. Hardy to −12° C.

PARENT COMPARISON

Plants of the new cultivar 'TURCAL139' are similar to the seed parent in most horticultural characteristics. 'TURCAL139', however, differs in the following:

1. Flower of the new variety are larger than flowers of the seed parent.
2. Flower color of the new variety is pink/salmon with a yellow center; flower color of the seed parent is pink/salmon with no yellow.

Plants of the new cultivar 'TURCAL139' are similar to the pollen parent in most horticultural characteristics. 'TURCAL139', however, differs in the following:

1. Flower color of the new variety is pink/salmon with a yellow center; flower color of the pollen parent is pink and white with a yellow throat.

COMMERCIAL COMPARISONS

Plants of the new cultivar 'TURCAL139' can be compared to the commercial variety *Alstroemeria* 'Valley Girl Compact', unpatented. Plants of these cultivars are similar in most horticultural characteristics, however, 'TURCAL139' differs in the following:

1. Flower color of the new variety is pink/salmon with a bright yellow blotch; flower color of this comparator is muted orange with a more pale yellow blotch.

2. The new variety is more cold hardy than this comparator.
3. Foliage color of the new variety not prone to turning yellow during the flowering period as observed in this comparator.

Plants of the new cultivar 'TURCAL139' can be compared to the commercial variety *Alstroemeria* 'Zapriliali', U.S. Plant Pat. No. 29,712. Plants of these cultivars are similar in most horticultural characteristics, however, 'TURCAL139' differs in the following:

1. Main flower color of the new variety is pink/salmon (Red 41C); main flower color of this comparator is light red-purple (Red-Purple 73C and 73D).
2. The new variety is more cold hardy than this comparator.
3. Foliage color of the new variety not prone to turning yellow during the flowering period as observed in this comparator.

Plants of the new cultivar 'TURCAL139' can be compared to the commercial variety *Alstroemeria* 'Tara', U.S. Plant Pat. No. 14,722. Plants of these cultivars are similar in most horticultural characteristics, however, 'TURCAL139' differs in the following:

1. Main flower color of the new variety is pink/salmon (Red 41C); main flower color of this comparator is medium pink (Red 45C).
2. Plants of the new variety are much shorter than plants of 'Tara', which are used for cut flower purposes. Plants of the new variety are approximately ⅓ the size of plants of 'Tara'.

BRIEF DESCRIPTION OF THE PHOTOGRAPHS

This new *Alstroemeria* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Alstroemeria*.

DETAILED BOTANICAL DESCRIPTION

Figure 1:
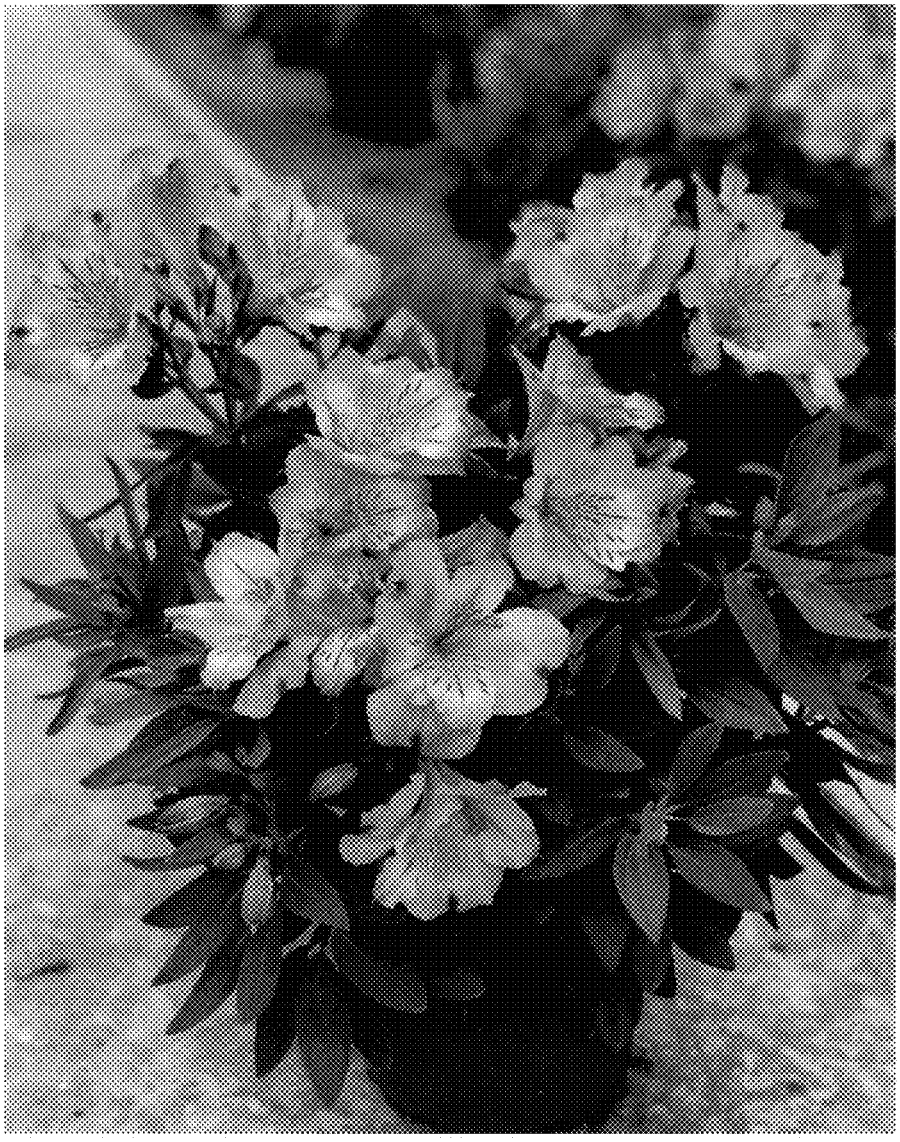
FIG. 1 is a color photograph of a flowering plant of 'TURCAL139' in a 12 cm during Summer in Gien, France. The plant is approximately 4 to 5 months old.
Figure 2:
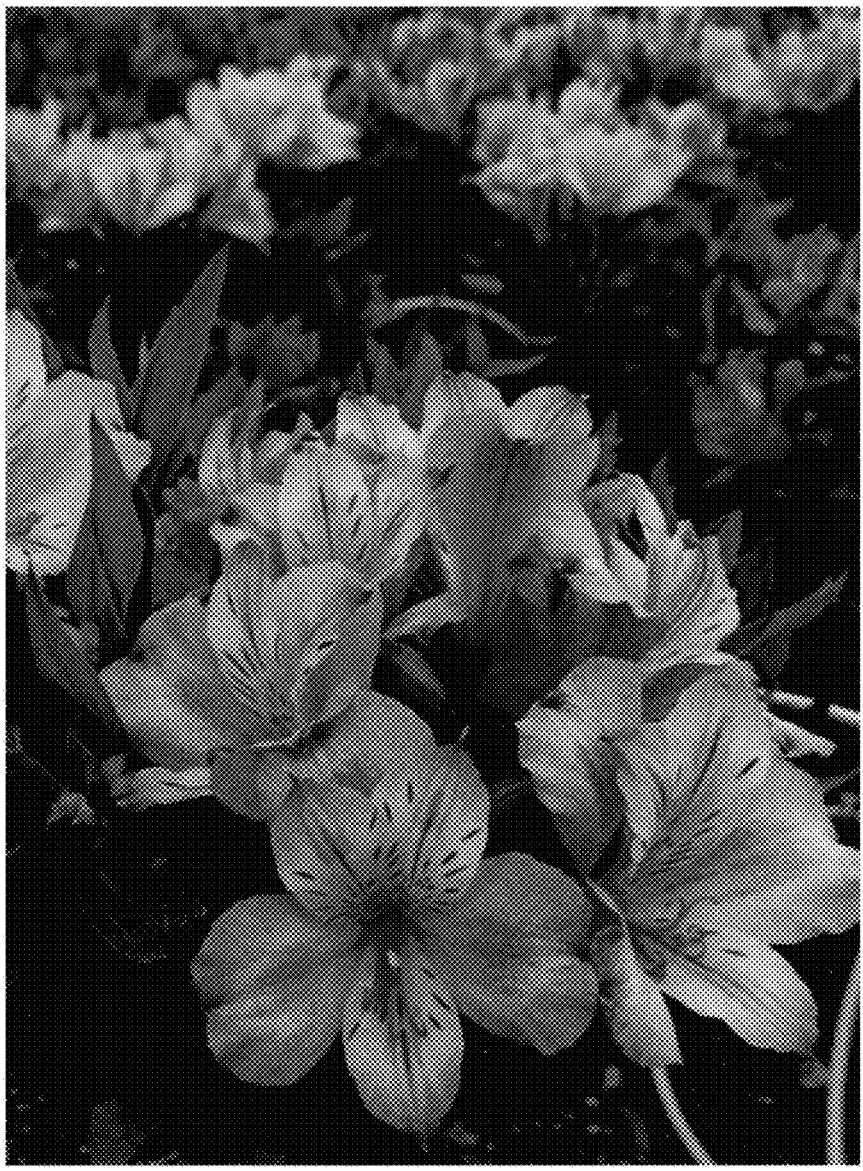
FIG. 2 is a color photograph showing a close-up view of an inflorescence of 'TURCAL139'

In the following description, color references are made to The Royal Horticultural Society Colour Chart 2015, except where general terms of ordinary dictionary significance are used. The following observations and measurements describe 'TURCAL139' plants grown in 12 cm pots in Gien, France. Plants were approximately 4 to 5 old. Temperatures ranged from approximately 3° C. to 22° C. at night and 10° C. to 32° C. during the day. No artificial light, photoperiodic treatments were given to the plants. No chemical treatments were given to plants. Measurements and numerical values represent averages of typical plant types.

Botanical classification: *Alstroemeria hybrida* 'TURCAL139'.

PROPAGATION

Method: Tissue culture.
Time to rooted plug: About 12 weeks to produce a 3 cm plug.
Root description: Fleshy and fibrous roots present. Cream colored.

PLANT

Growth habit: Compact, dwarf flowering perennial.
Height: 13 cm. At full mature height 25 to 30 cm.
Plant spread: 18 cm. At full mature width about 40 cm.
Stem characteristics: 9 primary basally emerging stems.
Length of stems: Approximately 10 cm.
Diameter of stems: Approximately 4 mm.
Texture of stems: Glabrous.
Color of stems: Near Green 137B and 137C streaked yellow-Green 145A and 145B. Base Greyed-Purple 183A.

FOLIAGE

Leaf:
- *Arrangement*.—Alternate.
- *Average length*.—Approximately 6 cm.
- *Average width*.—Approximately 2.4 cm.
- *Shape of blade*.—Obovate.
- *Apex*.—Acute.
- *Base*.—Truncate.
- *Margin*.—Entire.
- *Texture of top surface*.—Glabrous.
- *Texture of bottom surface*.—Glabrous.
- *Leaf internode length*.—1 cm.
- *Attachment*.—Sessile.
- *Color*.—Young foliage upper side: Near RHS Green 137A, 137B towards the base. Young foliage under side: Near RHS Green 137A, 137B towards the base. Mature foliage upper side: Near RHS Green 137A, 137B towards the base. Mature foliage under side: Near RHS Green 137A, 137B towards the base.
- *Venation*.—Type: Parallel. Venation color upper side: Yellow-Green 145A. Venation color under side: Yellow-Green 145A.

FLOWER

Natural flowering season: June to October.
Inflorescence type and habit: Single cup-shaped flowers arranged in umbels. Flowers outwardly facing.
Inflorescence size:
- *Diameter*.—Approximately 8 cm.
- *Heigh*.—Approximately 6 cm.

Inflorescences per plant: 5 to 6.
Flowers per inflorescence.—4 to 7.
Flower longevity on plant: About 7 days, after fully opened.
Flower size:
- *Diameter*.—Approximately 4.3 cm.
- *Length*.—Approximately 5 cm.

Perianth/petals:
- *Arrangement*.—Six arranged in two whorls, each whorl with two lateral and one median segment.
- *Inner lateral segment size*.—4.8 cm long and 1.8 cm wide. Shape: Ovate. Margin: Entire, very slightly undulate. Apex: Mucronate. Base: Attenuate. Texture: Glabrous. Color: When opening, upper side: Red 53B at the top, Yellow 4A in the center with stripes Greyed-Purple 183A. When opening, under side: Red 53A and Red 53B, mixed together. Yellow 4A in the center. Base Red-Purple 59A. Fully opened, upper side: Red 41C at the top with a hint of Red 53B at the tip. Yellow-Orange 14B in the center and faded to Red 41C at the base. Stripes are Greyed-Purple 183A. Stripes sparse in density. Fully opened under side: Red 41C at the top with a hint of Red 53B at the tip. Yellow-Orange 14B in the center and faded to Red 41C at the base.

*Outer lateral segment size*.—4 cm long and 2.9 cm wide. Shape: Wishbone-shaped. Margin: Entire, very slightly undulate. Apex: Mucronate. Base: Attenuate. Texture: Glabrous. Color: When opening, upper side: Red 50A. Center and base Yellow-Green 150D. Veins Green 138A. When opening, under side: Red 53A mixed with 53B. Tip Red 45C. Veins Green 138A. Fully opened, upper side: Red 41C mixed with Red 45C. Center Yellow 2D, base 2D with hint of 150B. Tip Red 53B and Yellow-Green 144A, Fully opened under side: Red 41C. Tip Red 53B and Yellow-Green 144A. Red 45C in the center.

*Outer median segment size*.—4 cm long and 2.8 cm wide. Shape: Spatulate Margin: Lower half entire, upper half finely dentate. Undulate. Apex: Mucronate. Base: Attenuate. Texture: Glabrous. Color: When opening, upper side: Red 50A. Center and base Yellow-Green 150D. Veins Green 138A. When opening, under side: Red 53A mixed with 53B. Tip Red 45C. Veins Green 138A. Fully opened, upper side: Red 41C mixed with Red 45C. Center Yellow 2D, base 2D with hint of 150B. Tip Red 53B and Yellow-Green 144A, Fully opened under side: Red 41C. Tip Red 53B and Yellow-Green 144A. Red 45C in the center.

Bud:

*Shape*.—Ovoid.
*Length*.—Approximately 1.5 cm.
*Diameter*.—Approximately 8 mm.
*Color*.—Near RHS Yellow-Green 145C flushed 145B and 145A towards the top. Hints of Red 53A.

Fragrance: None.

Peduncle:

*Length*.—1.2 to 2 cm.
*Diameter*.—3 mm.
*Color*.—Green 137B and 137C.
*Texture*.—Glabrous.

Pedicel:

*Length*.—1 cm.
*Diameter*.—2 mm.
*Color*.—Green 137B and 137C.
*Texture*.—Glabrous.

REPRODUCTIVE ORGANS

Stamens:

*Number*.—6.
*Filament length*.—Approximately 3 cm.
*Filament color*.—Near RHS Purple 71B, Yellow-Green 149D base.

Anthers:

*Length*.—5 mm.
*Color*.—Near RHS Yellow 12A.
*Pollen*.—Color: Near RHS Yellow 12A. Quantity: Moderate.

Pistil:

*Number*.—1.
*Length*.—Approximately 3.5 cm.
*Style*.—Length: Approximately 3 cm. Color: Near RHS Purple 71B, Yellow-Green 149D base.
*Stigma*.—Shape: 3-parted. Diameter: 7 mm. Color: Near RHS Red-Purple 71B. Ovary Color: Near RHS Green 137C.

OTHER CHARACTERISTICS

Fruit: Ovoid berry, approximately 4 mm in length and 4 mm in diameter. Colored RHS Blue 103D.

Seed: Not observed.

Disease/pest resistance: Neither resistance nor susceptibility to the normal diseases and pests of *Alstroemeria* has been observed.

Temperature tolerance: Cold hardy to −15°.

Drought tolerance: Tolerance for drought not tested.

What is claimed is:

1. A new and distinct cultivar of *Alstroemeria* plant named 'Turcal139' as herein illustrated and described.

* * * * *